United States Patent
Milioni De Carvalho et al.

(10) Patent No.: US 11,645,747 B2
(45) Date of Patent: May 9, 2023

(54) METHODS AND SYSTEMS FOR DIGITAL MAMMOGRAPHY IMAGING

(71) Applicant: GE Precision Healthcare LLC, Milwaukee, WI (US)

(72) Inventors: Pablo Milioni De Carvalho, Chaville (FR); Barbara Grosjean Leh, Orsay (FR); Jorge Corsino Espino, Paris (FR); Vincent Jonas Bismuth, Paris (FR)

(73) Assignee: GE Precision Healthcare LLC, Milwaukee, WI (US)

(*) Notice: Subject to any disclaimer, the term of this patent is extended or adjusted under 35 U.S.C. 154(b) by 363 days.

(21) Appl. No.: 16/801,042

(22) Filed: Feb. 25, 2020

(65) Prior Publication Data
US 2021/0264590 A1 Aug. 26, 2021

(51) Int. Cl.
G06T 7/00 (2017.01)
A61B 6/00 (2006.01)
G06T 5/00 (2006.01)

(52) U.S. Cl.
CPC .......... G06T 7/0012 (2013.01); A61B 6/502 (2013.01); G06T 5/003 (2013.01); G06T 2207/10116 (2013.01); G06T 2207/10144 (2013.01); G06T 2207/20182 (2013.01); G06T 2207/20201 (2013.01); G06T 2207/30068 (2013.01)

(58) Field of Classification Search
None
See application file for complete search history.

(56) References Cited

U.S. PATENT DOCUMENTS

| | | | |
|---|---|---|---|
| 7,295,691 B2 | 11/2007 | Uppaluri | |
| 7,440,634 B2* | 10/2008 | Ben-Ezra | H04N 23/683 |
| | | | 382/284 |
| 7,756,407 B2* | 7/2010 | Raskar | H04N 23/689 |
| | | | 348/208.99 |
| 8,390,704 B2* | 3/2013 | Wang | G06T 5/003 |
| | | | 348/248 |

(Continued)

FOREIGN PATENT DOCUMENTS

| | | | |
|---|---|---|---|
| JP | 2004174232 A | 6/2004 | |
| JP | 2012096084 A | 5/2012 | |

(Continued)

OTHER PUBLICATIONS

S. Mijovic and M. Dakovic, "Feature extraction from mammograms by using a'priory information," 2013 2nd Mediterranean Conference on Embedded Computing (MECO), 2013, pp. 144-147, doi: 10.1109/MECO.2013.6601341 (Year: 2013).*

Dirk Robinson M et al: "Efficient Fourier-Wavelet Super-Resolution", IEEE Transactions on Image Processing, Service Center, Piscataway, NJ, US, vol. 19, No. 10, Oct. 1, 2010 (Oct. 1, 2010), pp. 2669-2681, XP011328615, ISSN: 1057-7149, DOI: 10.1109/TIP.2010.2050107.

(Continued)

*Primary Examiner* — Vu Le
*Assistant Examiner* — Courtney Joan Nelson
(74) *Attorney, Agent, or Firm* — McCoy Russell LLP (57) ABSTRACT

Various methods and systems are provided for reducing blur in a diagnostic image. In one example, a method includes reducing blur in a diagnostic image by applying a deconvolution filter to the diagnostic image, the deconvolution filter generated from a point spread function (PSF) estimation of blur at each pixel of the diagnostic image, the PSF estimation generated based on a motion vector field between the diagnostic image and a pre-shot image acquired prior to the diagnostic image.

14 Claims, 5 Drawing Sheets

(56) References Cited

U.S. PATENT DOCUMENTS

| | | | |
|---|---|---|---|
| 2012/0314093 A1 | 12/2012 | Tamayama | |
| 2013/0182928 A1* | 7/2013 | Park | G06T 5/50 |
| | | | 382/131 |
| 2015/0063545 A1* | 3/2015 | Lee | G16H 30/40 |
| | | | 378/91 |
| 2015/0157288 A9* | 6/2015 | Ren | A61B 8/13 |
| | | | 600/410 |
| 2015/0359502 A1* | 12/2015 | Zou | A61B 6/5235 |
| | | | 378/101 |
| 2016/0019678 A1* | 1/2016 | Cecil | A61B 6/5211 |
| | | | 378/62 |
| 2020/0193570 A1* | 6/2020 | Aoki | G06T 5/50 |

FOREIGN PATENT DOCUMENTS

| | | | | |
|---|---|---|---|---|
| JP | 2013003610 A | | 1/2013 | |
| WO | WO-2013174425 A1 | * | 11/2013 | ............. G06K 9/481 |

OTHER PUBLICATIONS

EP application 21156139.4 filed Feb. 9, 2021—Extended Search Report dated Jul. 30, 2021; 10 pages.

Kamona Nada et al: "Automatic detection of simulated motion blur in mammograms", Medical Physics., [Online] vol. 47, No. 4, Mar. 5, 2020 (Mar. 5, 2020), pp. 1786-1795, XP055824032, US ISSN: 0094-2405, DOI: 10.1002/mp.14069 Retrieved from the Internet: URL:https://onlinelibrary.wiley.com/doi/full-xml/10.1002/mp.14069; retrieved on Jul. 14, 2021].

JP patent application 2021-024573 filed Feb. 18, 2021—Decision of Refusal dated Oct. 19, 2022; Machine Translation; 3 pages.

JP2012096084 English Abstract, Espacenet search results Dec. 19, 2022; 1 page.

JP application 2021-024573 filed Feb. 18, 2021—Office Action dated Apr. 13, 2022; Machine Translation, 4 pages.

\* cited by examiner

METHODS AND SYSTEMS FOR DIGITAL MAMMOGRAPHY IMAGING

FIELD

Embodiments of the subject matter disclosed herein relate to medical imaging, and more particularly to digital mammography imaging.

BACKGROUND

Mammography is a medical imaging procedure that includes x-ray images for detecting the presence of one or more tumors or lesions in a breast. In digital mammography, a scout or pre-shot image may be taken of a patient to determine an x-ray technique (e.g., x-ray tube current and voltage, exposure time) to acquire images of the patient having a sufficient brightness. Upon determination of the x-ray technique, one or more x-ray images of the patient may be acquired. In some examples, multiple x-ray images may be acquired at different view angles and/or at different energy levels.

BRIEF DESCRIPTION

In one embodiment, a method includes reducing blur in a diagnostic image by applying a deconvolution filter to the diagnostic image, the deconvolution filter generated from a point spread function (PSF) estimation of blur at each pixel of the diagnostic image, the PSF estimation generated based on a motion vector field between the diagnostic image and a pre-shot image acquired prior to the diagnostic image.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

The following description relates to various embodiments for digital mammography imaging procedures. Digital mammography imaging procedures may include acquiring 2-dimensional (2D) or 3D digital images of the breast. For example, digital breast tomosynthesis (DBT) is an imaging technique for generating cross-sectional images of a breast at high in-plane resolution. During imaging using a digital mammography system, the breast is compressed and low dose x-ray projection images of the breast at one or more x-ray tube angles may be obtained at a detector. The projection images are then reconstructed as either standard 2D images, or the multiple images at different angles may be used to construct a 3D volume from which 2D slices may be obtained.

However, during x-ray exposure, patient motion may occur which may induce blur artifacts (e.g., blurring) within the reconstructed image. Blurring may obscure significant breast pathology and can necessitate repeat imaging, thus increasing the radiation dose received by patients and raising patient anxiety. Steps may be taken to reduce patient motion such as improving patient positioning, limiting the potential of patient movement, and arresting respiration for the exposure duration, yet blurring may still persist. Blur may occur as a result of inadequate breast compression, patient muscle relaxation, compression paddle movement, and/or patient movement.

Thus, according the embodiments disclosed herein, a method is provided that estimates motion vectors at each image pixel by registering a pre-shot image (hypothetically with no motion; very short acquisition) and a diagnostic, full dose mammography image. The motion vector field can generate Point Spread Functions (PSF) of blur, at each image pixel. The estimated PSF can then be used to deconvolve motion blur and improve spatial resolution. The image registration may be configured to estimate motion vectors in high-noise images, and thus may be robust even using pre-shot images, which are typically high noise images. By leveraging this technique in pre-shot (noisy) vs full dose mammography images, a motion kernel may be estimated, which can be used to deconvolve motion blur in the full dose mammography images.

Figure 1:
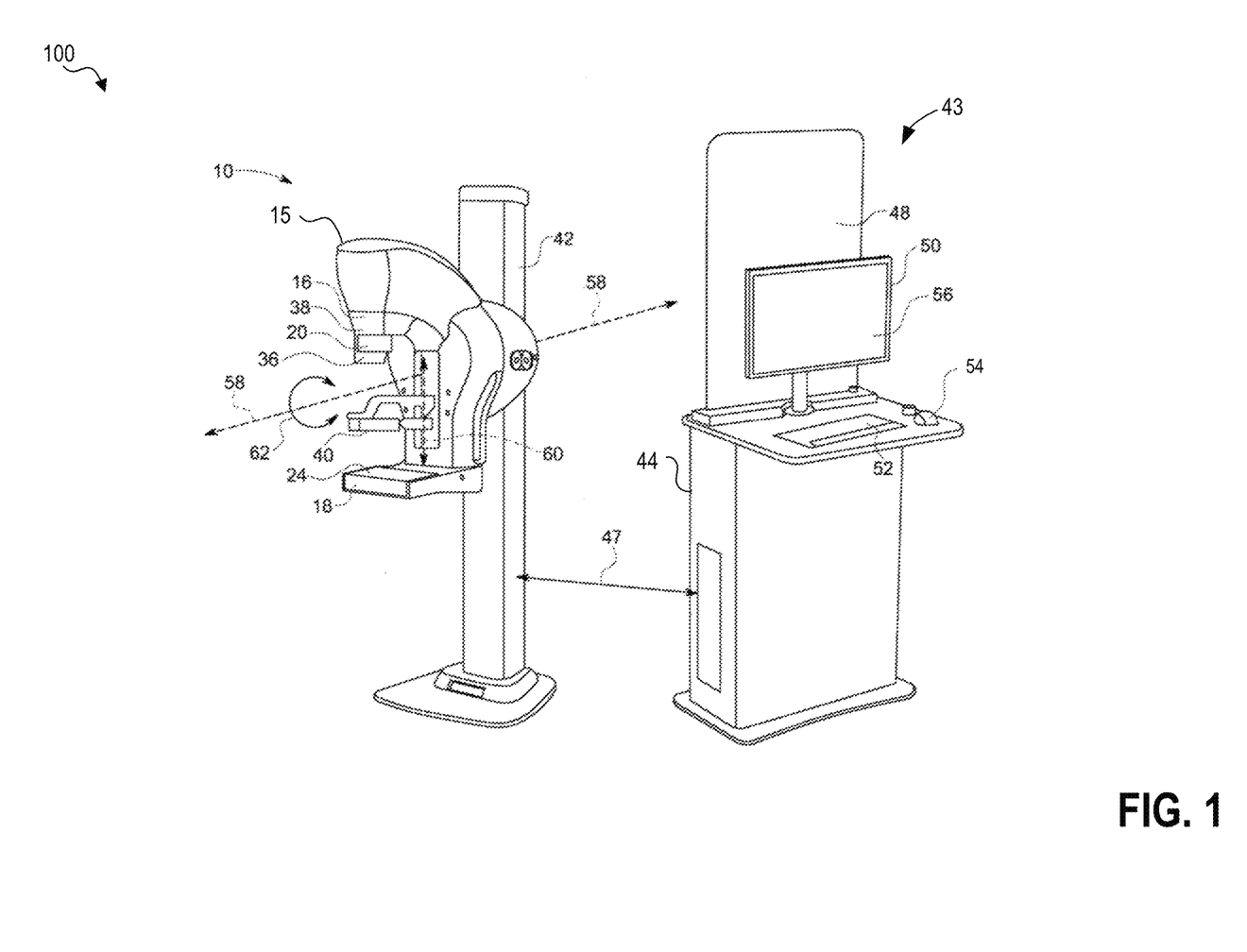
FIG. 1 is a schematic illustration of a digital mammography system according to an embodiment.
Figure 2:
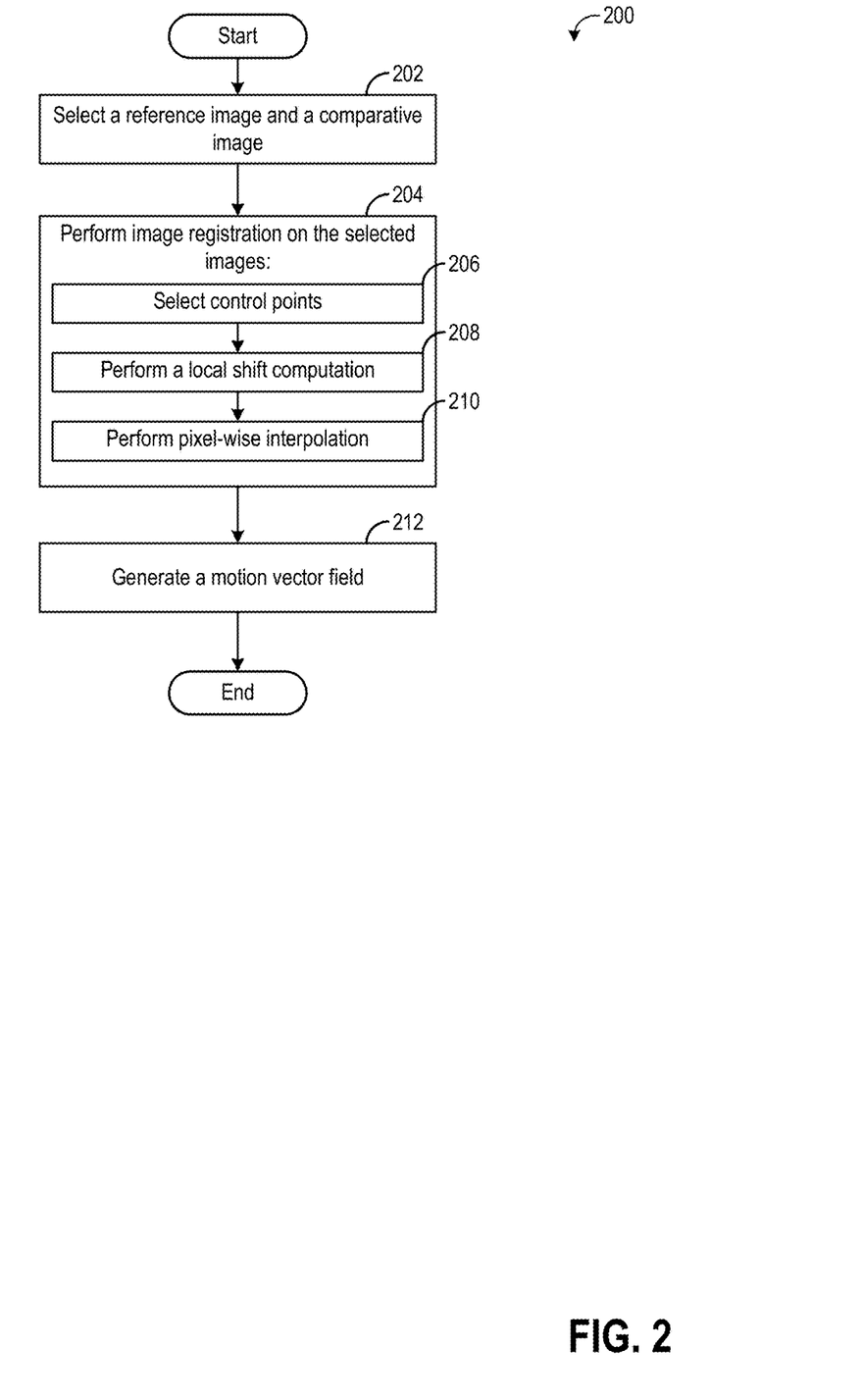
FIG. 2 is an image registration method according to an embodiment.
Figure 3:
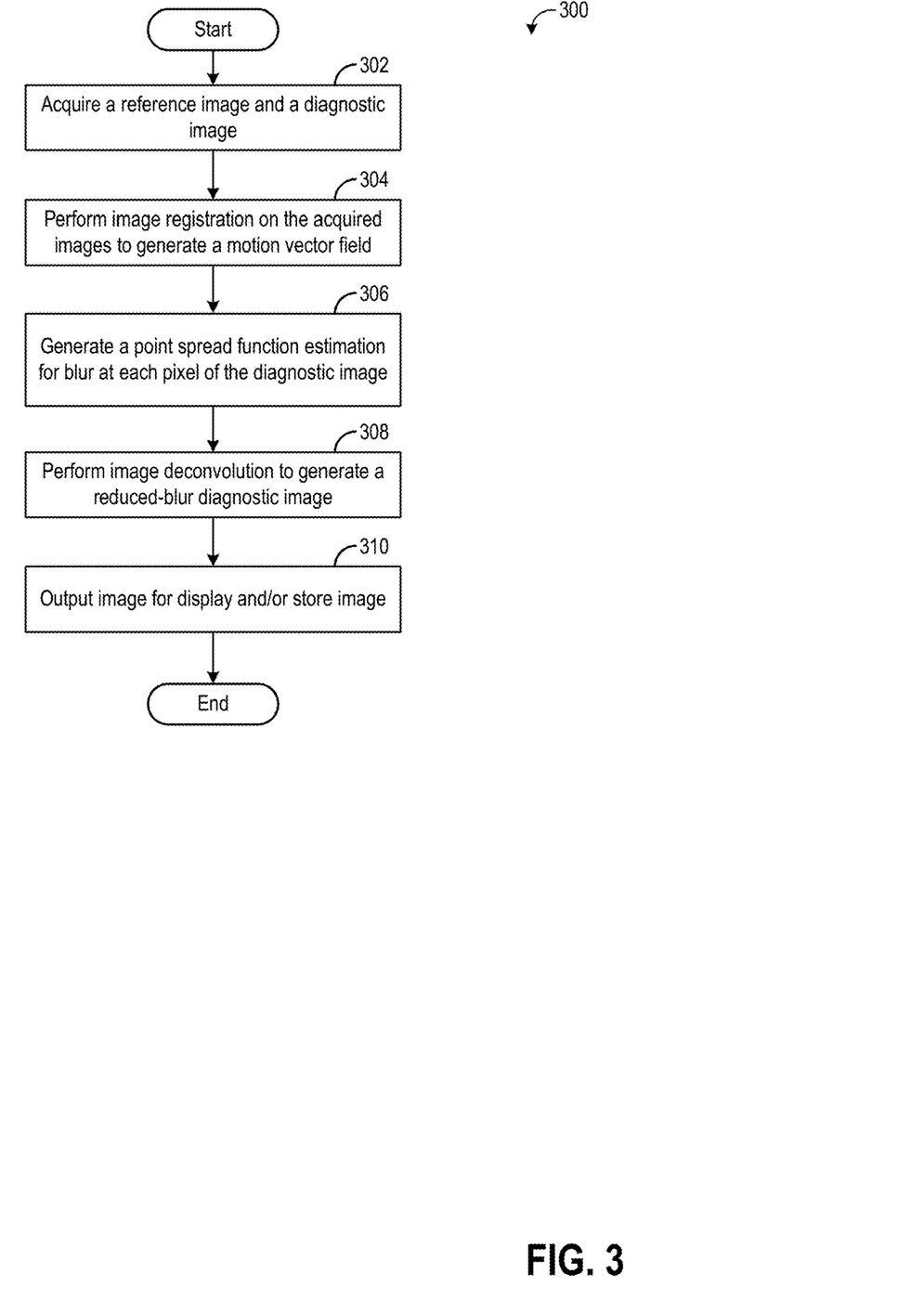
FIG. 3 is a flow chart of a method for detecting and reducing the effects of patient motion induced blur within digital mammography generated images according to embodiments disclosed herein.

FIG. 1 is a schematic illustration of a digital mammography system which may be used to acquire diagnostic x-ray images of a patient. FIG. 2 is an image registration method that may be applied to images acquired with the digital mammography system of FIG. 1, as shown schematically by the process of FIG. 4. FIG. 3 is a flow chart of a method for reducing blur within x-ray images using a motion vector field generated according to the method of FIG. 2, as shown schematically by the process of FIG. 5.

Referring to FIG. 1, a digital mammography system 100 including an x-ray system 10 for performing a mammography procedure is shown, according to an embodiment of the disclosure. In some examples, the x-ray system 10 may be a tomosynthesis system, such as a digital breast tomosynthesis (DBT) system. In some examples, the x-ray system 10 may be configured to acquire dual-energy images, which may facilitate increased visualization of certain structures (e.g., vasculature) when the patient is injected with a contrast agent. Further, the x-ray system 10 may be used to perform one or more procedures including digital tomosynthesis imaging, and DBT guided breast biopsy.

The x-ray system 10 includes a support structure 42, to which a radiation source 16, a radiation detector 18, and a collimator 20 are attached. The radiation source 16 is housed within a gantry 15 that is movably coupled to the support structure 42. In particular, the gantry 15 may be mounted to the support structure 42 such that the gantry 15 including the radiation source 16 can rotate around an axis 58 in relation to the radiation detector 18. An angular range of rotation of the gantry 15 housing the radiation source 16 indicates a rotation up to a desired degree on either directions about the axis 58. For example, the angular range of rotation of the radiation source 16 may be −θ to +θ, where θ may be such that the angular range is a limited angle range, less than 360 degrees. An exemplary x-ray system may have an angular range of ±11 degrees, which may allow rotation of the gantry (that is rotation of the radiation source) from −11 degrees to +11 degrees about an axis of rotation of the gantry. The angular range may vary depending on the manufacturing specifications. For example, the angular range for DBT systems may be approximately ±11 degrees to ±60 degrees, depending on the manufacturing specifications. In some examples, the gantry 15 may be fixed and may not rotate.

The radiation source 16 is directed toward a volume or object to be imaged, and is configured to emit radiation rays at desired times to acquire one or more images. The radiation detector 18 is configured to receive the radiation rays via a surface 24. The detector 18 may be any one of a variety of different detectors, such as an x-ray detector, digital radiography detector, or flat panel detector. The collimator 20 is disposed adjacent to the radiation source 16 and is configured to adjust an irradiated zone of a subject.

In some embodiments, the system 10 may further include a patient shield 36 mounted to the radiation source 16 via face shield rails 38 such that a patient's body part (e.g., head) is not directly under the radiation. The system 10 may further include a compression paddle 40, which may be movable upward and downward in relation to the support structure along a vertical axis 60. Thus, the compression paddle 40 may be adjusted to be positioned closer to the radiation detector 18 by moving the compression paddle 40 downward toward the detector 18, and a distance between the detector 18 and the compression paddle 40 may be increased by moving the compression paddle upward along the vertical axis 60 away from the detector. The movement of the compression paddle 40 may be adjusted by a user via compression paddle actuator (not shown) included in the x-ray system 10. The compression paddle 40 may hold a body part, such as a breast, in place against the surface 24 of the radiation detector 18. The compression paddle 40 may compress the body part, and hold the body part still in place while optionally providing apertures to allow for insertion of a biopsy needle, such as a core needle, or a vacuum assisted core needle. In this way, compression paddle 40 may be utilized to compress the body part to minimize the thickness traversed by the x-rays and to help reduce movement of the body part due to the patient moving. The x-ray system 10 may also include an object support (not shown) on which the body part may be positioned.

The digital mammography system 100 may further include workstation 43 comprising a controller 44 including at least one processor and a memory. The controller 44 may be communicatively coupled to one or more components of the x-ray system 10 including one or more of the radiation source 16, radiation detector 18, the compression paddle 40, and a biopsy device. In an embodiment, the communication between the controller and the x-ray system 10 may be via a wireless communication system. In other embodiments, the controller 44 may be in electrical communication with the one or more components of the x-ray system via a cable 47. Further, in an exemplary embodiment, as shown in FIG. 1, the controller 44 is integrated into workstation 43. In other embodiments, the controller 44 may be integrated into one or more of the various components of the system 10 disclosed above. Further, the controller 44 may include processing circuitry that executes stored program logic and may be any one of a different computers, processors, controllers, or combination thereof that are available for and compatible with the various types of equipment and devices used in the x-ray system 10.

The workstation 43 may include a radiation shield 48 that protects an operator of the system 10 from the radiation rays emitted by the radiation source 16. The workstation 43 may further include a display 50, a keyboard 52, mouse 54, and/or other appropriate user input devices that facilitate control of the system 10 via a user interface 56.

Controller 44 may adjust the operation and function of the x-ray system 10. As an example, the controller 44 may provide timing control, as to when the x-ray source 16 emits x-rays, and may further adjust how the detector 18 reads and conveys information or signals after the x-rays hit the detector 18, and how the x-ray source 16 and the detector 18 move relative to one another and relative to the body part being imaged. The controller 44 may also control how information, including images 42 and data acquired during the operation, is processed, displayed, stored, and manipulated. Various processing steps as described herein with respect to FIGS. 2 and 3, performed by the controller 44, may be provided by a set of instructions stored in non-transitory memory of controller 44.

Further, as stated above, the radiation detector 18 receives the radiation rays 22 emitted by the radiation source 16. In particular, during imaging with the x-ray system, a projection image of the imaging body part may be obtained at the detector 18. In some embodiments, data, such as projection image data, received by the radiation detector 18 may be electrically and/or wirelessly communicated to the controller 44 from the radiation detector 18. The controller 44 may then reconstruct one or more x-ray images based on the projection image data, by implementing a reconstruction algorithm, for example. The reconstructed image may be displayed to the user on the user interface 50 via a display screen 56.

The radiation source 16, along with the radiation detector 18, forms part of the x-ray system 10 which provides x-ray imagery for the purpose of one or more of screening for abnormalities, diagnosis, dynamic imaging, and image-guided biopsy. For example, the x-ray system 10 may be operated in a mammography mode for screening for abnormalities. During mammography, a patient's breast is positioned and compressed between the detector 18 and the compression paddle 40. Thus, a volume of the x-ray system 10 between the compression paddle 40 and the detector 18 is an imaging volume. The radiation source 16 then emits radiation rays on to the compressed breast, and a projection image of the breast is formed on the detector 18. The projection image may then be reconstructed by the controller 44, and displayed on the interface 50. During mammography, the gantry 15 may be adjusted at different angles to obtain images at different orientations, such as a craniocaudal (CC) image and a medio-lateral oblique (MLO) image. In one example, the gantry 15 may be rotated about the axis 58 while the compression paddle 40 and the detector 18 remain stationary. In other examples, the gantry 15, the compression paddle 40, and the detector 18 may be rotated as a single unit about the axis 58.

Further, the x-ray system 10 may be operated in a tomosynthesis mode for performing digital breast tomosynthesis (DBT). During tomosynthesis, the x-ray system 10 may be operated to direct low-dose radiation towards the imaging volume (between the compression paddle 40 and the detector 18) at various angles over the angular range of the x-ray system 10. Specifically, during tomosynthesis, similar to mammography, the breast is compressed between the compression paddle 40 and the detector 18. The radiation source 16 is then rotated from −θ to +θ, and a plurality of projection images of the compressed breast is obtained at regular angular intervals over the angular range. For example, if the angular range of the x-ray system is ±11 degrees, 22 projection images may be captured by the detector during an angular sweep of the gantry at approximately one every one degree. The plurality of projection images are then processed by the controller 44 to generate a plurality of DBT image slices. The processing may include applying one or more reconstruction algorithms to reconstruct three dimensional image of the breast. Furthermore, the x-ray system may be configured to perform a DBT-guided biopsy procedure. Accordingly, in some exemplary embodiments, the system 10 may further include a biopsy device comprising a biopsy needle for extracting a tissue sample for further analysis.

In some examples, digital mammography system 100 may be configured to perform contrast imaging where contrast agents, such as iodine, can be injected into the patient that travel to the region of interest (ROI) within the breast (e.g., a lesion). The contrast agents are taken up in the blood vessels surrounding a cancerous lesion in the ROI, thereby providing a contrasting image for a period of time with respect to the surrounding tissue, enhancing the ability to locate the lesion.

The use of a contrast agent can be coupled with images of the ROI taken using dual-energy imaging processes and technology. In dual-energy imaging, low-energy (LE) and high-energy (HE) images are taken of the ROI. In particular, contrast enhanced spectral mammography (CESM) (2D) and contrast enhanced digital breast tomosynthesis (CE-DBT) (3D) imaging modalities are performed with dual-energy technology. For each view (single view in CESM, multiple views for CE-DBT), a pair of images is acquired: a low-energy (LE) image and a high-energy (HE) image. In CE-DBT, non-paired HE and LE images may be acquired for each view and an HE volume, LE volume, and recombined CE volumes may be reconstructed for the ROI. For example, the HE and LE views may be interleaved during the CE-DBT scan (alternatively HE, LE, HE, LE, HE, LE, etc.) with a switch from HE to LE then to HE again etc., for each angulated position of the x-ray tube. The LE and HE images are usually obtained at mean energies above and below the K-edge of the contrast agent. At x-ray energies just above the k-edge of the contrast agent, the absorption of x-rays is increased resulting in an increase of contrast from the iodine contrast agent in the HE image.

In dual-energy 3D or stereotactic procedures, LE and HE image acquisitions are performed, with at least two different positions of the X-ray source with respect to the detector. The images are then recombined to display material-specific information with regard to the internal structure of the tissue being imaged. In the case of 3D CESM, for example, after the injection of contrast medium, dual-energy images are acquired at two or more positions of the x-ray tube with respect to the detector. For each of these tube angulations, the low and high-energy images are recombined to produce an image of the contrast medium surface concentration at each pixel to provide an iodine-equivalent or dual-energy (DE) image(s) (for a single view in CESM, and for multiple views for CE-DBT), which in CE-DBT, are used to reconstruct a 3D volume. Image recombination may be performed based on simulations of the X-ray image chain, via calibrations on a reference phantom, or any other suitable 3D-reconstruction process. Additionally, in the continuous mode of acquisition where the X-ray tube moves continuously with interleaved HE and LE images being taken, the LE images are used to reconstruct a LE 3D volume, and the HE images are used to reconstruct a HE 3D volume, with both volumes being recombined in a suitable manner to provide an iodine 3D volume. One can as well implement an algorithm that combines 3D-reconstruction and HE/LE recombination in a single step.

FIG. 2 is an image registration method 200 that may be applied to images acquired by a digital mammography system (e.g. digital mammography system 100 of FIG. 1) to compare or integrate data obtained within different images from an image set. In some examples, image registration may be used as a preliminary step in other image processing applications, such as the method of de-blurring images generated from the digital mammography system described herein (see FIG. 3). Method 200 may be executed using computer readable instructions stored in the non-transitory memory of a computing device of a digital mammography system (e.g., digital mammography system 100 of FIG. 1) or a controller communicatively coupled to the digital mammography system (e.g., controller 44 of FIG. 1). In some embodiments, method 300 may be executed by another computing device without departing from the scope of this disclosure (e.g., an edge device, a picture archiving and communication system (PACS)).

At 202, a reference image and a comparative image may be selected from an image set acquired by the digital mammography system. In some examples, more than one comparative image may be selected. The reference image herein may be defined as the image to which the comparative image (or images) is aligned via during image registration. The reference image may be a pre-shot image (when the image registration method is performed to reduce blur in an image according to the method of FIG. 3) and the comparative image may be a diagnostic image taken at a time subsequent to the pre-shot image. In other examples, such as during dual energy imaging, the reference image may be a low-energy image and the comparative image may be a high-energy image. The reference image and the comparative image may be images of the same anatomical features/scan plane of the same patient.

At 204, image registration may be performed on the selected images. During image registration, the comparative image may be aligned to the reference image via a spatial domain method. The spatial domain method may include selecting control points within the reference image and the comparative image at 206. The control points may be individual pixels or groups of neighboring pixels. The control points may be selected randomly in one example. In another example, the control points may be selected based on a predefined grid or other pattern. In a still further example, the control points may be selected based on which pixels/anatomical regions of the comparative image are likely to exhibit motion-based blurring, such as pixels at edges of anatomical structures. The control points may be at the same location in each of the reference image and the comparative image.

At 208, a local shift computation may be performed between the control points of the two images. The local shift computation may indicate, for each control point of the comparative image, the magnitude and direction of shift of that control point relative to the reference image. For example, the local shift computation may generate a motion vector that comprises the vector difference between the position x,y (for rows and columns) of the same clinical/anatomical feature (e.g., a micro calcification or a lesion) in the two images: $dx=x1-x2$, $dy=y1-y2$.

At 210, pixel-wise interpolation may be performed based on the local shift computation. The interpolation may include a first interpolation that is performed to pass from the motion vectors at each control point to a motion vector field with motion vectors at every image pixel (e.g., the pixel wise interpolation 409 in FIG. 4). The first interpolation may include B-spline interpolation or another suitable interpolation. Thus, the first interpolation may include a B-spline interpolation to generate a motion vector field, as indicated 212, where the motion vector field includes a respective motion vector at every pixel based on the motion vectors at the control points and may be used to reduce image blur, as explained below. During image registration, a second interpolation may be performed where, for every pixel p (xp, yp) in the comparative image (e.g., the image that is being registered), the vector field value at pixel p (dx,dy) is used to retrieve the image pixel value in position (xp+dx, yp+dy) in the same image (because that is where the pixel is supposed to be, according to the reference image). Since dx and dy are not integer values, interpolation is performed on the surrounding pixels using a linear or cubic function, for example, which may create a registered image.

FIG. 3 is a flow chart of a method 300 for reducing patient motion-induced blur within x-ray images (e.g., digital mammography images) according to embodiments disclosed herein. Method 300 may be executed using computer readable instructions stored in the non-transitory memory of a computing device of a digital mammography system (e.g., digital mammography system 100 of FIG. 1) or a controller communicatively coupled to the digital mammography system (e.g., controller 44 of FIG. 1). In some embodiments, method 300 may be executed by another computing device without departing from the scope of this disclosure (e.g., an edge device, a picture archiving and communication system (PACS)).

At 302, a reference image and a diagnostic image may be acquired by the digital mammography system. The reference image may be a pre-shot image. The pre-shot image may be a short exposure, low dose image that may have a relatively high amount of noise, and thus may not be suitable for use in diagnostic imaging purposes, but may be used to ensure proper patient positioning, calculate the full dosage needed to acquire images of a target brightness, etc. The diagnostic image may be a full dose diagnostic image taken after the pre-shot image. In this way, the diagnostic image may be acquired at a higher radiation dose than the pre-shot image and/or for a longer exposure duration.

At 304, image registration may be performed on the acquired images to generate a motion vector field. The image registration may be performed according to the method of FIG. 2 explained above (e.g., with the diagnostic image being the comparative image described with respect to FIG. 2). The image registration may output a motion vector field that includes an estimated motion vector for each pixel of the diagnostic image relative to the pre-shot image.

At 306, a point spread function (PSF) estimation for blur at each pixel of the diagnostic image may be generated based on the motion vector field. The PSF may be estimated based on the motion vector field obtained from the image registration between the reference image and the comparative image. For example, for every image pixel, a chosen function f(p) may be fit using the surrounding motion vector values (from the motion field). This function is the PSF.

At 308, image deconvolution is performed to generate an image with reduced blur. For example, based on the PSF, a deconvolution filter may be generated and applied to the diagnostic image, resulting in an image with reduced blur. For example, the image may be convolved with a filter calculated from the inverse of the PSF. At 310, the image (e.g., after application of the deconvolution filter) is output for display on a display device (e.g., display 50) and/or stored in memory of a computing device (e.g., a memory of controller 44 or on a PACS or other suitable image stored device). Method 300 then ends.

In some examples, method 300 may be performed on all diagnostic images acquired with the digital mammography system. In other examples, method 300 may be performed only in response to a user request to deblur an image. For example, after a diagnostic image is acquired, the diagnostic image may be displayed to a user (e.g., a technologist or other clinician). The user may determine that an unacceptable amount of blur is present and may enter an input (e.g., via a touchscreen, keyboard, etc.) requesting the deblur process of method 300 be applied to reduce the blur in the diagnostic image. In still other examples, method 300 may be performed only in response to a determination (e.g., by the digital mammography system or other computing device) that a diagnostic image is blurry, which may be based on a sharpness of edges, an artificial-intelligence based model, or another suitable mechanism.

Further, while method 300 was described above as being performed by a digital mammography system, and thus the diagnostic image described above may be an image of breast tissue, method 300 may be performed on other types of x-ray images, such as lung images. In such examples, method 300 may be executed on a different type of x-ray imaging system, such as a chest x-ray imaging system.

Figure 4:
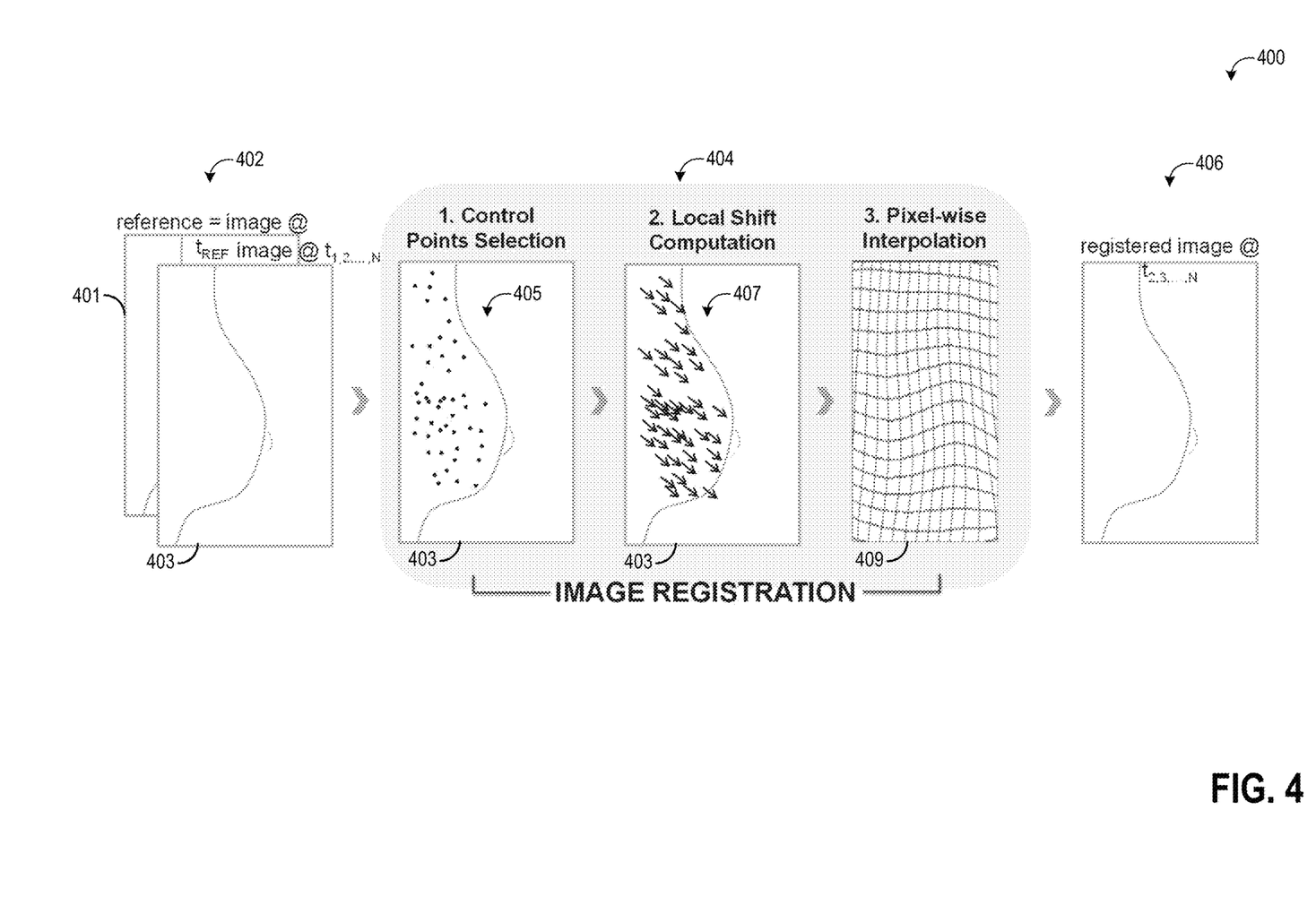
FIG. 4 schematically shows a process for image registration.

FIG. 4 schematically shows an example image registration process 400 according to an embodiment of the disclosure. The image registration process 400 shown in FIG. 4 may be carried out according to the method of FIG. 2. The image registration process 400 includes the registration of two images, shown at 402. The two images include a reference image 401 and a comparative image 403. The reference image 401 may be acquired at an earlier point in time than the comparative image 403. As explained above, the reference image may be a pre-shot image while the comparative image may be a full dose diagnostic image.

At 404, the two images are registered by selecting control points, computing a local shift at each control point, and performing a pixel-wise interpolation. Example control points 405 and example local shift vectors 407 are shown on comparative image 403. As appreciated by FIG. 4, the local shift computation may include determination of a vector quantifying direction and magnitude of motion/shift for each control point of the comparative image relative to the corresponding control point of the reference image. The pixels of the comparative image are then interpolated on a pixel-wise basis using an interpolation grid 409. Each pixel may be interpolated based on the pixel values of neighboring pixels and the motion vectors as described above. The output of the image registration process 400 is a registered image 406, which may in some examples be the comparative image 403 with adjustments made to some pixels in order to register (e.g., align) features of the comparative image 403 with the reference image 401.

Figure 5:
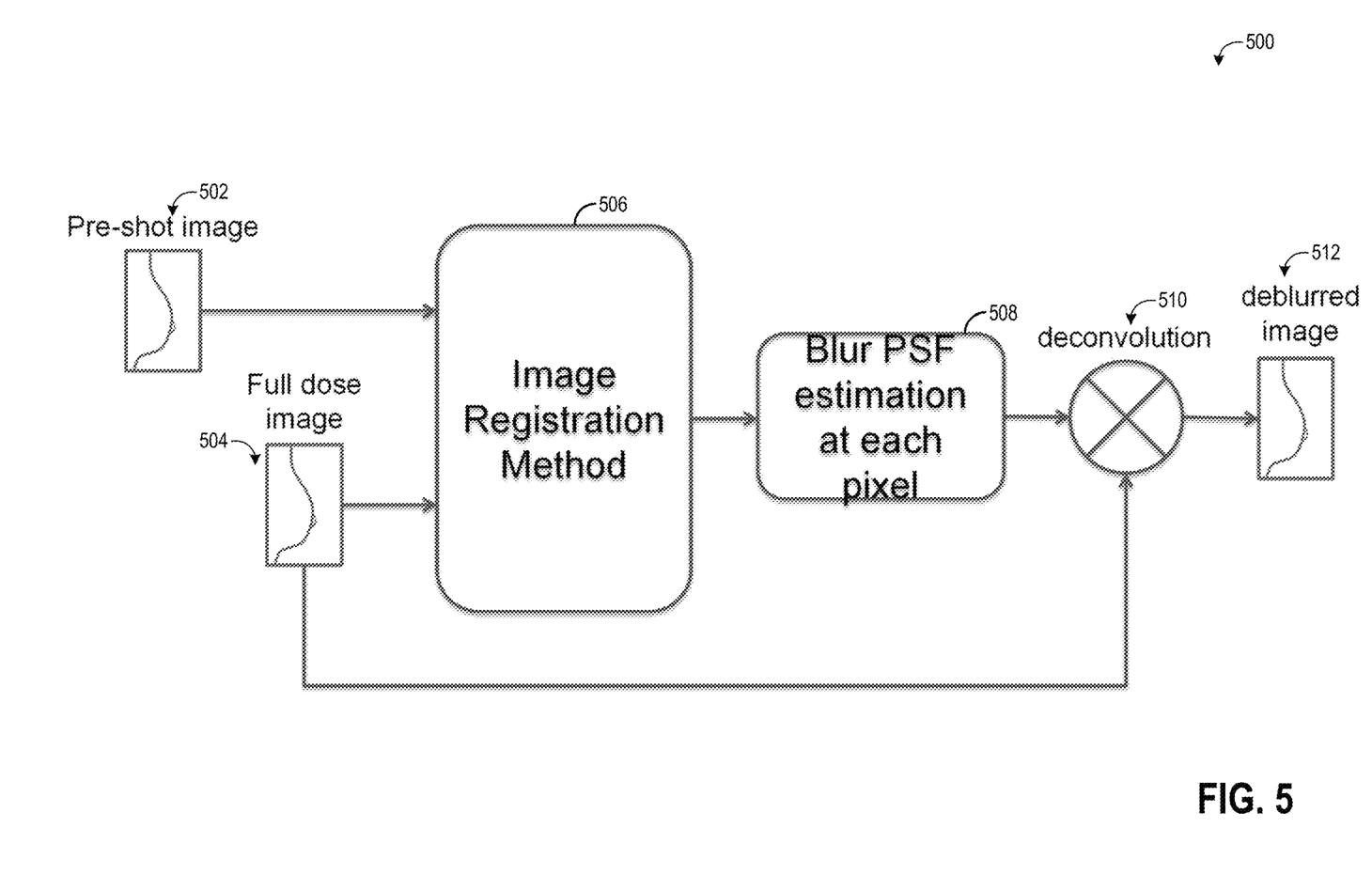
FIG. 5 schematically shows a process for reducing blur.

FIG. 5 shows an example deblurring process 500 according to an embodiment of the disclosure. The deblurring process 500 may be carried out according to the method 300 of FIG. 3 in order to reduce motion-based image blurring that may occur due to patient movement during x-ray exposure. The deblurring process 500 includes entering a pre-shot image 502 and a full dose image 504 into an image registration method 506. The pre-shot image 502 may be acquired before the full dose image 504 and may be acquired at a lower radiation dose and/or for a shorter exposure time. As a result, it is assumed that no motion occurred during acquisition of the pre-shot image, thus allowing the pre-shot image to be a fixed image to which the full dose image 504 may be compared. The full dose image 504 may be acquired with a longer exposure time and thus may be prone to motion-based blurring. To reduce the blur in the full dose image 504, the full dose image 504 is registered to the pre-shot image 502 using the image registration method described above with respect to FIG. 2 and shown schematically in FIG. 4.

The output from the image registration process 506 may be a motion vector field that may be used to estimate a point spread function (PSF) at each pixel, as shown at 508. Based on the PSF for each pixel, a deconvolution filter is generated, which is applied to the full dose image at 510. The deconvolution of the full dose image results in a deblurred image 512, which may be output for display and/or stored in memory as part of a patient exam.

The technical effect of using a pre-shot image as a reference image for deblurring a full dose, diagnostic image is decreased motion-based image blur and more accurate imaging of patient anatomical features.

An embodiment relates to a method, including reducing blur in a diagnostic image by applying a deconvolution filter to the diagnostic image, the deconvolution filter generated from a point spread function (PSF) estimation of blur at each pixel of the diagnostic image, the PSF estimation generated based on a motion vector field between the diagnostic image and a pre-shot image acquired prior to the diagnostic image. In a first example of the method, the diagnostic image is an x-ray image acquired with an x-ray imaging system at a first, higher x-ray radiation dose, and the pre-shot image is an x-ray image acquired with the x-ray imaging system at a second, lower x-ray radiation dose. In a second example of the method, which optionally includes the first example, the diagnostic image is acquired with a first, longer x-ray radiation exposure and the pre-shot image is acquired with a second, shorter x-ray radiation exposure. In a third example of the method, which optionally includes one or both of the first and second examples, the first x-ray radiation dose is determined based on a brightness of the pre-shot image and the second x-ray radiation dose. In a fourth example of the method, which optionally includes one or more or each of the first through third examples, the method further includes outputting the reduced blur diagnostic image for display on a display device. In a fifth example of the method, which optionally includes one or more or each of the first through fourth examples, the method further includes generating the motion vector field by selecting a plurality of control points in the pre-shot image, calculating a local shift vector for each control point relative to a corresponding control point in the diagnostic image, and interpolating each pixel of the diagnostic image based on each local shift vector to generate the motion vector field.

An embodiment of a method includes acquiring, with an x-ray imaging system, a pre-shot image of a patient and a diagnostic image of the patient; generating a motion vector field by registering the diagnostic image to the pre-shot image; applying a deconvolution filter to the diagnostic image to generate a reduced-blur diagnostic image, the deconvolution filter generated based on the motion field vector; and outputting the reduced-blur diagnostic image for display on a display device. In a first example of the method, the diagnostic image is acquired with the x-ray imaging system at a first, higher x-ray radiation dose, and the pre-shot image is acquired with the x-ray imaging system at a second, lower x-ray radiation dose. In a second example of the method, which optionally includes the first example, the diagnostic image is acquired with a first, longer x-ray radiation exposure and the pre-shot image is acquired with a second, shorter x-ray radiation exposure. In a third example of the method, which optionally includes one or both of the first and second examples, the first x-ray radiation dose is determined based on a brightness of the pre-shot image. In a fourth example of the method, which optionally includes one or more or each of the first through third examples, the deconvolution filter is generated based on the motion vector field by estimating a point spread function for each pixel of the diagnostic image based on the motion vector field and generating the deconvolution filter based on each point spread function. In a fifth example of the method, which optionally includes one or more or each of the first through fourth examples, generating the motion vector field comprises selecting a plurality of control points in the pre-shot image, calculating a local shift vector for each control point relative to a corresponding control point in the diagnostic image, and interpolating each pixel of the diagnostic image based on each local shift vector to generate the motion vector field.

An embodiment of an imaging system includes an x-ray source in communication with a detector; a display device; and a computing device connected in communication with the display device and the detector, the computing device including a processor and non-transitory memory storing instructions executable by the processor to: acquire, with the x-ray source and detector, a pre-shot image of a patient at a first x-ray dose and for a first exposure duration; acquire, with the x-ray source and detector, a diagnostic image of the patient at a second, higher x-ray dose and for a second, longer exposure duration; correct blur in the diagnostic image based on the pre-shot image to generate a reduced-blur diagnostic image; and output the reduced-blur diagnostic image for display on the display. In a first example of the system, correcting blur in the diagnostic image based on the pre-shot image comprises estimating a respective motion vector for one or more pixels of the diagnostic image via a registration process with the pre-shot image; and applying a deconvolution filter to the diagnostic image to generate a reduced-blur diagnostic image, the deconvolution filter generated based on each respective motion vector. In a second example of the system, which optionally includes the first example, generating the deconvolution filter comprises generating a point spread function for each pixel of the diagnostic image based on each respective motion vector and generating the deconvolution filter based on each point spread function. In a third example of the system, which optionally includes one or both of the first and second examples, the second x-ray dose is determined based on a brightness of the pre-shot image and the first x-ray dose.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
reducing blur in a diagnostic image by applying a deconvolution filter to the diagnostic image, the deconvolution filter generated from a point spread function (PSF) estimation of blur at each pixel of the diagnostic image, the PSF estimation generated based on a motion vector field between the diagnostic image and a pre-shot image acquired prior to the diagnostic image, wherein the diagnostic image is an x-ray image acquired with an x-ray imaging system at a first, higher x-ray radiation dose, and the pre-shot image is an x-ray image acquired with the x-ray imaging system at a second, lower x-ray radiation dose.

2. The method of claim 1, wherein the diagnostic image is acquired with a first, longer x-ray radiation exposure and the pre-shot image is acquired with a second, shorter x-ray radiation exposure.

3. The method of claim 1, wherein the first x-ray radiation dose is determined based on a brightness of the pre-shot image and the second x-ray radiation dose.

4. The method of claim 1, further comprising outputting the reduced blur diagnostic image for display on a display device.

5. The method of claim 1, further comprising generating the motion vector field by selecting a plurality of control points in the pre-shot image, calculating a local shift vector for each control point relative to a corresponding control point in the diagnostic image, and interpolating each pixel of the diagnostic image based on each local shift vector to generate the motion vector field.

6. A method, comprising:
acquiring, with an x-ray imaging system, a pre-shot image of a patient and a diagnostic image of the patient, wherein the diagnostic image is acquired with a first, longer x-ray radiation exposure and the pre-shot image is acquired with a second, shorter x-ray radiation exposure;
generating a motion vector field by registering the diagnostic image to the pre-shot image;
applying a deconvolution filter to the diagnostic image to generate a reduced-blur diagnostic image, the deconvolution filter generated based on the motion vector field; and
outputting the reduced-blur diagnostic image for display on a display device.

7. The method of claim 6, wherein the diagnostic image is acquired with the x-ray imaging system at a first, higher x-ray radiation dose, and the pre-shot image is acquired with the x-ray imaging system at a second, lower x-ray radiation dose.

8. The method of claim 7, wherein the first x-ray radiation dose is determined based on a brightness of the pre-shot image.

9. The method of claim 6, wherein the deconvolution filter is generated based on the motion vector field by estimating a point spread function for each pixel of the diagnostic image based on the motion vector field and generating the deconvolution filter based on each point spread function.

10. The method of claim 6, wherein generating the motion vector field comprises selecting a plurality of control points in the pre-shot image, calculating a local shift vector for each control point relative to a corresponding control point in the diagnostic image, and interpolating each pixel of the diagnostic image based on each local shift vector to generate the motion vector field.

11. An imaging system, comprising:
an x-ray source in communication with a detector;
a display device; and
a computing device connected in communication with the display device and the detector, the computing device including a processor and non-transitory memory storing instructions executable by the processor to:
acquire, with the x-ray source and detector, a pre-shot image of a patient at a first x-ray dose and for a first exposure duration;
acquire, with the x-ray source and detector, a diagnostic image of the patient at a second, higher x-ray dose and for a second, longer exposure duration;
correct blur in the diagnostic image based on motion between the pre-shot image and the diagnostic image to generate a reduced-blur diagnostic image; and
output the reduced-blur diagnostic image for display on the display.

12. The imaging system of claim 11, wherein correcting blur in the diagnostic image based on the pre-shot image comprises estimating a respective motion vector for one or more pixels of the diagnostic image via a registration process with the pre-shot image; and applying a deconvolution filter to the diagnostic image to generate a reduced-blur diagnostic image, the deconvolution filter generated based on each respective motion vector.

13. The imaging system of claim 12, wherein generating the deconvolution filter comprises generating a point spread function for each pixel of the diagnostic image based on each respective motion vector and generating the deconvolution filter based on each point spread function.

14. The imaging system of claim 11, wherein the second x-ray dose is determined based on a brightness of the pre-shot image and the first x-ray dose.

* * * * *